(12) United States Patent
Zadrozny et al.

(10) Patent No.: US 6,540,674 B2
(45) Date of Patent: Apr. 1, 2003

(54) SYSTEM AND METHOD FOR SUPERVISING PEOPLE WITH MENTAL DISORDERS

(75) Inventors: Wlodek W. Zadrozny, Tarrytown, NY (US); Dimitri Kanevsky, Ossining, NY (US)

(73) Assignee: IBM Corporation, Armonk, NY (US)

( * ) Notice: Subject to any disclaimer, the term of this patent is extended or adjusted under 35 U.S.C. 154(b) by 136 days.

(21) Appl. No.: 09/751,531

(22) Filed: Dec. 29, 2000

(65) Prior Publication Data

US 2002/0087052 A1 Jul. 4, 2002

(51) Int. Cl.[7] .............................. A61B 5/00; G08B 23/00
(52) U.S. Cl. ................... 600/300; 340/573.1; 340/573.4
(58) Field of Search ................................ 600/300, 301; 705/2, 3; 340/573.1, 573.4

(56) References Cited

U.S. PATENT DOCUMENTS

| | | | |
|---|---|---|---|
| 5,696,492 A | * | 12/1997 | Sakamaki et al. ........ 340/573.1 |
| 6,198,394 B1 | * | 3/2001 | Jacobsen et al. ........ 340/573.1 |
| 6,221,010 B1 | * | 4/2001 | Lucas ........................ 600/300 |
| 6,238,337 B1 | * | 5/2001 | Kambhatla et al. ........ 600/300 |
| 6,377,296 B1 | | 4/2002 | Zlatsin et al. |
| 6,421,453 B1 | | 7/2002 | Kanevsky et al. |

FOREIGN PATENT DOCUMENTS

GB      2285135 A   *  6/1995

* cited by examiner

*Primary Examiner*—Eric F. Winakur
*Assistant Examiner*—David J. McCrosky
(74) *Attorney, Agent, or Firm*—Dilworth & Barrese, LLP (57) ABSTRACT

A system and method for supervising persons with a mental illness, the method comprising the steps of acquiring sensor data related to the person and the person's environment; tracking the acquired sensor data; and recognizing changes in the sensor data indicating the occurrence of an event. The method further comprises the steps of acquiring access to an event database of stored event data entries, each event data entry comprising identification of one of the sensor means, identification of the entity being sensed by the sensor means, and allowable values for the sensor data and recommendations for assistance providing actions to be taken when the received sensor data is out of range from the allowable sensor data; and recognizing the occurrence of an incident in which the received sensor data is outside of the range of the stored allowable sensor data values.

32 Claims, 3 Drawing Sheets

SYSTEM AND METHOD FOR SUPERVISING PEOPLE WITH MENTAL DISORDERS

FIELD OF THE INVENTION

This invention relates to a system and method for supervising people with mental disorders, and in particular, to a system and method of applying tracking and look-up methods for supervising the actions and conditions of people with mental illness and disabilities.

BACKGROUND OF THE INVENTION

People with mental illnesses, such as Alzheimer's Disease, depression, mental retardation and substance dependency often require supervision, typically performed by a guardian. Supervision is necessary for monitoring the actions and behaviors of the mentally ill person to aid them in functioning in and out of the home, to monitor their medicinal intake and to guard them from danger. Due to memory loss, disorientation and/or subaverage intellectual functioning, mentally ill people frequently have difficulty with self care, traveling to familiar or unfamiliar locations, and with occupational or recreational activities. In certain cases a mentally ill person may pose a danger to himself and others. Supervision of a mentally ill person, in varying degrees, is necessary for providing the person with a source of advice, a source of information, monitoring of his actions and behaviors, monitoring of the condition of the person, monitoring of the medicinal intake of the person, monitoring of compliance with supplied directions, diffusing problematic situations and detecting dangerous situations.

Typically, the need for full time supervision of a mentally ill person is fulfilled at home by a family member, detracting from the family member's ability to fulfill their other responsibilities, or by a hired aide, creating a financial burden. Alternatively, supervision is provided by placing the mentally ill person in an institution, thus limiting the freedom of the mentally ill person and incurring great cost to the person's family or the government.

Furthermore, mentally ill persons who have been released from a care-giving facility in order to return to normal activities, require supervision of proper medicinal intake for preventing a return of symptoms. By providing limited supervision of a functioning person with a mental illness, a recurrence of symptom presentation can be avoided.

There are cases in which a mental illness is suspected, or is confirmed and possibly progressing. By examining the activities of persons functioning at various levels the existence or progression of an illness can be monitored. Upon determination of a progression of an illness, proper intervention by medical professionals can be provided. Thus, further progression is prevented by providing the proper medications at appropriate doses.

In addition, individuals with medical issues and/or their caretakers find it cumbersome to follow a regimented schedule of medications, blood testing, urine testing, required feedings, etc., while attempting to maintain normal activities. Supervision of a schedule, including reminders, can provide the support needed for proper maintenance medical care.

There exists a need for a system and method for providing various levels of supervision of a mentally ill person. There further exists a need for a centralized system for providing supervision of a plurality of mentally ill persons at the same or at different locations.

SUMMARY

It is an aspect of this invention to provide a system and a method for supervising a mentally ill person.

It is another aspect of this invention to provide a system and a method for recognizing events, which pose a danger to a mentally ill person.

It is another aspect of this invention to provide a system and a method for providing assistance to a mentally ill person.

It is another aspect of this invention to provide a system and a method for monitoring progression of a mental illness.

It is another aspect of this invention to provide a centralized system for providing supervision of a plurality of mentally ill persons at the same or at different locations.

To accomplish the above and other aspects, a method is proposed for supervising a person with a mental illness, which, in the preferred embodiment comprises the steps of acquiring sensor data related to the person and the person's environment; tracking the acquired sensor data; and recognizing changes in the sensor data indicating the occurrence of an event. The method further comprises acquiring access to an event database of stored event data entries, each event data entry comprising identification of one of the sensor means, identification of the entity being sensed by the sensor means, and allowable values for the sensor data and recommendations for assistance providing actions to be taken when the received sensor data is out of range from the allowable sensor data; and recognizing the occurrence of an incident in which the received sensor data is outside of the range of the stored allowable sensor data values. The method further comprises the steps of receiving requests for information related to recognized events; processing the requests; and retrieving the requested information from the event database and outputting the retrieved information. The method further comprises the steps of retrieving a stored recommendation upon recognition of the occurrence of an incident and providing the assistance recommended to a user interface. The method further comprises the step of tracking the progression of the disease of the individual.

In addition, a system is proposed for supervising a person with a mental illness, which, in the preferred embodiment, comprises sensor means for sensing physical entities relating to the person and the person's environment, the sensor means outputting sensor data; a user interface receiving sensor data and user requests; and a Supervision Provider Server in communication with the user interface. The Supervision Provider Server comprises an event data base for storing event data, wherein each event data entry comprises an identification of one of the sensor means, identification of the entity being sensed by the sensor means, allowable values for the sensor data and recommendations for cases in which sensor data is outside of the range of the allowable values. The Supervision Provider Server further comprises means for tracking the sensor data; means for recognizing a change in the sensor data indicating the occurrence of an event; means for recognizing the occurrence of an incident in which the sensor data is outside of the range of the stored allowable values; means for retrieving the stored recommendations upon the occurrence of an event; and means for providing assistance recommended in the recommendations to the user interface. The Supervision Provider Server further comprises means for processing requests for information related to recognized events and means for retrieving the requested information from the event database.

DETAILED DESCRIPTION OF THE INVENTION

In the following description, the terms "server" and "database" are used in a generic functional sense. The term "server" should be understood within the client/server architectural model—the client requests a service, the server provides a service. The term "database" can be understood in its broad definition as a data structure storing different pieces of hardware. A "database" and "server" may be depicted as one entity labeled a "database" which is inclusive of the "server" functions to provide access to the database. Indeed any of the servers or databases could be implemented using a distributed network system, where the functional elements of a server or database are not only distributed among nodes, but will often migrate from node to node. On the opposite end of the spectrum, all of the servers and databases discussed below could be resident on one mainframe computer. However much of each server or database is implemented in software, firmware or hardware being also open to many variations, as is well known in the art.

Furthermore the terms "network" and "computer" are used in the most general sense. A "computer" is any computing means, from a single microprocessor or micro controller to a computer system distributed over multiple processing nodes. A "network" includes any means that connects computers. Thus, although the preferred embodiment uses the Internet, the nodes could connect through any other type of Intranet or network such as a central server with individual point-to-point connections, a LAN, etc.

Other terms in the text are also to be understood in a generic functional sense, as would be known by one skilled in the art.

Figure 1:
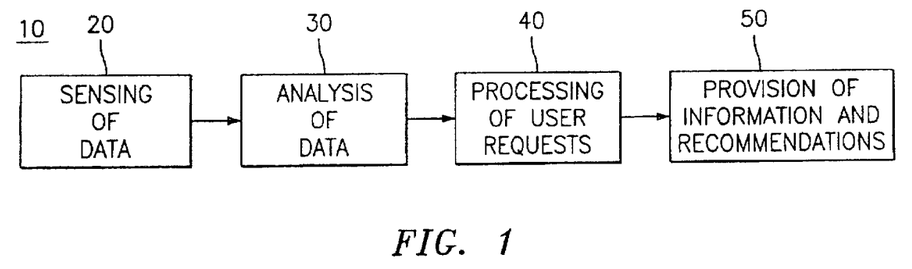
FIG. 1 is a block diagram of the fundamental modules of a preferred embodiment of the present invention.

The system 10, according to the preferred embodiment of the present invention, is depicted in FIG. 1. In the first stage, Sensing of Data 20, the activities, environment, and physical condition of a person are sensed, and sensor data is provided. The second stage, Analysis of Data 30, involves processing and analyzing the sensor data, and recognizing the occurrence of events. In the third stage, Processing of User Requests 40, requests entered by users are processed. In the final stage, Provision of Information and Recommendations 50, information and recommendations are provided to the user and the person responsive to requests and recognized events.

Although the final three stages will be described in the preferred embodiment as being managed by one entity, provided with data from the first stage, each stage could be handled by a separate entity. In other words, in the preferred embodiment, a single service provider is managing the final three stages for subscribers. It is preferable that the data gather in Sensing of Data Stage 20 is provided to the other three stages over the Internet. It is also contemplated that for more local uses, the data is provided over a LAN or similar network.

Figure 2:
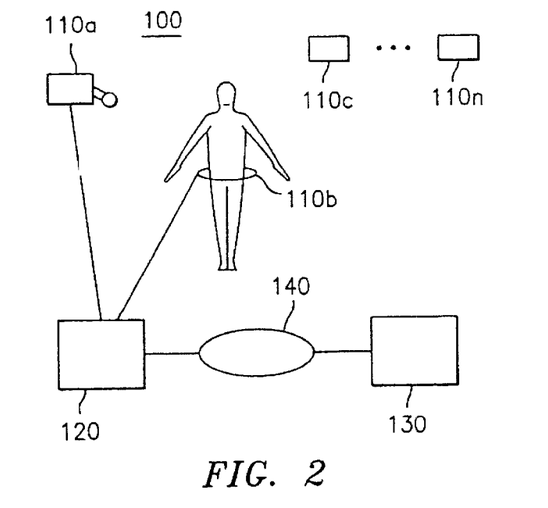
FIG. 2 is a diagram of a system according to the preferred embodiment of the present invention.

FIG. 2 is a diagram depicting the preferred embodiment of the system 100 for providing the services shown in FIG. 1. As shown, a plurality of sensor means 110a–n are provided for sensing actions of a person with a mental illness, the physical condition of the person, the condition of the environment of the person, and objects in the environment of the person. Sensor means 110a is preferably a camera recording visual and audio data. Sensor means 110b is preferably a bio-sensor or plurality of biosensors sensing the physical condition of the person, and may be physically attached to the person. Sensor means 110c–n are additional sensors sensing physical entities of the environment, such as additional cameras, thermometers, smoke detectors, etc.

In the preferred embodiment, sensor means 110a–n include portable sensors to be used with a mentally ill person who is moving from location to location. Portable sensors function to provide necessary data to the system 100 for supervising and assisting the person while allowing the person to travel. For example, a portable sensor can detect a red light or a dangerous situation such as an oncoming car. In addition, portable sensors preferably aide in the navigation of the person. Examples of portable sensors include optical, tactile, audio, motion and directional sensors as well as devices such as an odometer for sensing and measuring distance traveled. Sensory devices are commercially available for supervising and assisting blind people as they travel.

A user interface 120 is provided for allowing a user, such as a guardian, and/or the mentally ill person to communicate with a Supervision Provider Server (SP) 130. In the preferred embodiment the user interface 120 and SP 130 are in communication via a network 140, preferably the Internet. In yet another embodiment, it is contemplated that the user interface 120 and the SP 130 are embodied as a single entity whereby the SP 130 is located at the site of the mentally ill person. In yet another embodiment, it is also contemplated that the user interface 120 and SP 130 are combined into a single unit such as a hand held device in another embodiment of the present invention. It is also further contemplated that the services provided by the SP 130 are distributed between the user interface 120 and the SP 130. The sensor means 110a–n are in communication with the user interface 120, either directly, or in another embodiment, the data produced by the sensor means 110a–n is manually provided to the user interface 120 by user entry or by peripheral data storage means such as a CD-ROM. Alternatively the sensor data, or a portion of the sensor data, is sent directly to the SP 130. Furthermore, sensor means 110a–n, which are internal to the SP 130, such as a clock, are provided.

In the preferred embodiment, the user interface 120 receives data input from the sensor means 110a–n and provides the data to the SP 130. The user interface 120 receives personal data about the user or guardian and the mentally ill person for registration and for updating the personal data. The user interface 120 provides the personal data to the SP 130. In addition, the user interface 120 receives requests input from the user or the mentally ill person and transmits the requests to the SP 130 for processing. The user interface 120 receives output from the SP 130 and communicates the output to the user or directly to the mentally ill person.

Requests are input into the user interface 120 via input mediums such as a microphone for receiving audio requests; a camera for receiving gesture requests; a computer input device such as a keyboard, touch screen, etc. The user interface 120 uses recognition techniques such as speech recognition software (ASR) and a gesture recognition system for recognizing received requests. Gesture recognition is disclosed in U.S. Pat. No. 6,421,453, having the same assignee as the present application, entitled "Apparatus and Method for User Recognition Employing Behavioral Passwords," the disclosure of which is incorporated herein by reference.

The user interface 120 communicates output from the SP 130 to the user or mentally ill person via output means. Examples of output means include: speakers for transmitting audio information; a screen or monitor for transmitting visual information such as graphics, text, lights, alarms, beepers, vibrators, devices etc. for transmitting signals, alarms and information. Each output from the SP 130 can be transformed into the proper form for being transmitted via various output means, as needed to suit the user/mentally ill person. For example, text can be translated into speech via voice synthesis or into graphics. The output means can be custom made for the system or can be commercially available devices.

The SP 130 is a server for receiving sensor data and user requests via the user interface 120; recognizing events within the sensor data; analyzing the sensor data; and providing information and recommendations to the user and/or the person via the user interface 120 responsive to the sensor data and the user requests. The SP 130 comprises modules residing on one or more computers. The SP 130 preferably further comprises modules for communicating with personnel for providing further analysis.

The SP 130 preferably requires that use of the service provided be limited to individuals who have registered with the system. Upon registering, users of the system enter personal and financial data to be used for administration purposes. Furthermore, upon registering, users enter personal data about the mentally ill person and his environment. The personal data about the mentally ill person and his environment is entered via the user interface 120 at registration, at the beginning of a supervision session and on an ongoing basis as needed.

As defined above, the mentally ill person and/or user, i.e. the guardian or supervisor, may be an individual or a plurality of individuals. The SP 130 receives sensor data associated with a plurality of mentally ill persons at a plurality of locations for providing simultaneous, real time supervision of a plurality of mentally ill persons. The service provided by the SP is provided either for gratis or for a fee. Preferably the fee is variable according to the degree of services requested and used by the user/person.

Figure 3:
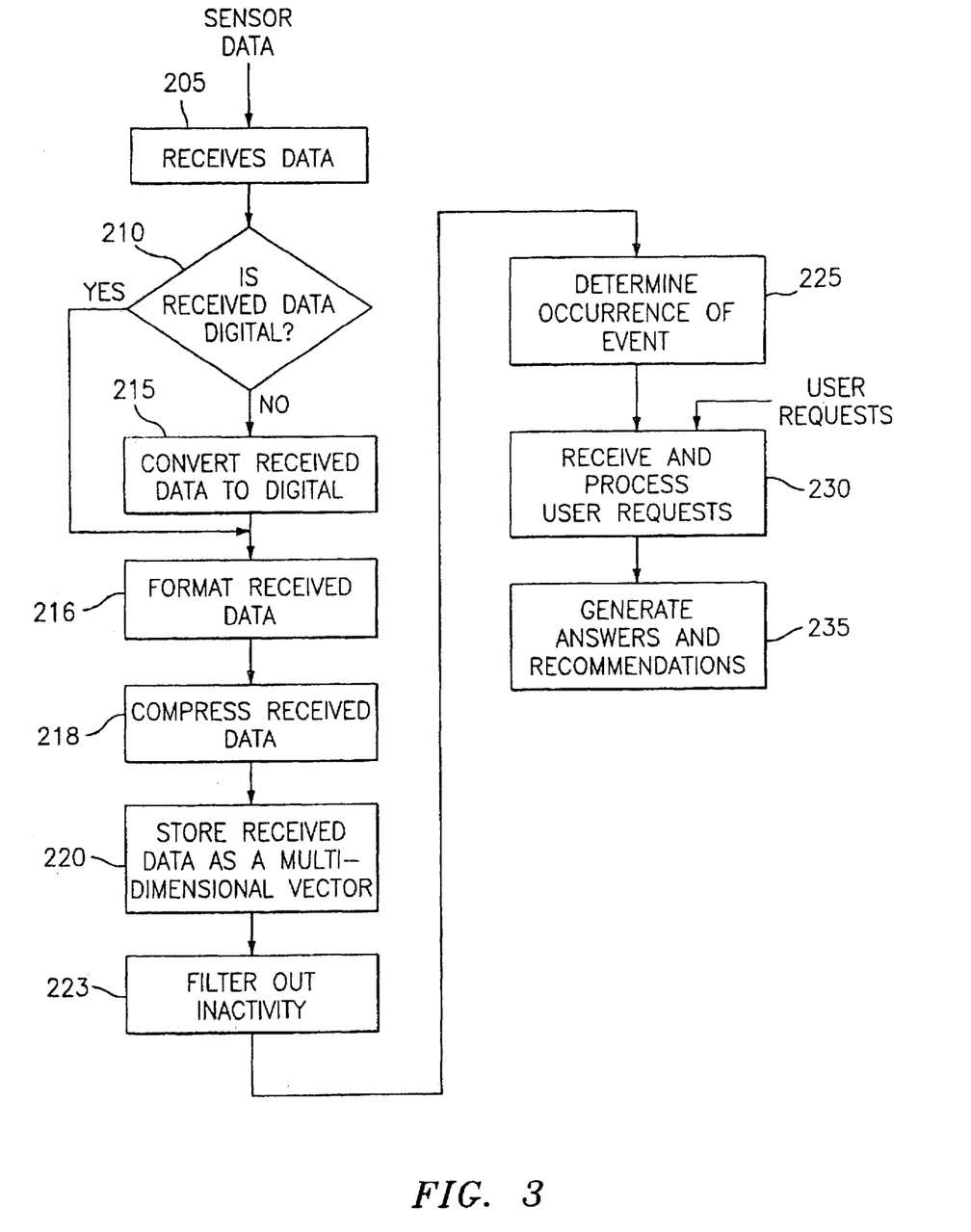
FIG. 3 is a flowchart of a method according to the preferred embodiment of the present invention.

A general outline of the basic steps performed by the SP 130 in the preferred embodiment of the present system is shown in FIG. 3. At step (205) the SP 130 receives data provided by the sensor means 110a–n. The sensor data is preferably provided by the user interface, however it is possible that it is provided directly by the sensor means 110. The sensor data is continuously received on a real time basis. At step (210) it is determined whether or not the received data is digital data. If not, the received sensor data is converted into digital form at step (215). The digitized data is stored in formatted files at step (216).

Digital data comprising large amounts of data, such as an image and/or audio recording comprising a series of frames, is compressed at step (218). Data compression functions to preserve space and to provide a schematic representation of the recording, which can be broken down for analysis. In the preferred embodiment the file is compressed by sampling the series of frames at regular intervals and storing the sampled frames with a time stamp. Alternatively, sampling is done at irregular intervals. The sampled recording frames are then formatted and stored as multidimensional vectors at step (220). Before storing the sampled frames, it is preferable to filter out inactivity at step (223). Any known method can be employed for digitizing, compressing and storing the data. According to preference, the order of compressing and formatting and digitizing can be rearranged.

For cases in which the SP 130 is receiving sensor data for a person from multiple sensors, the sensor data includes a sensor type identifier and category identifier for identifying the type and category respectively of the sensor providing data. Examples of sensor types include pulse, temperature, camera-video, camera-audio, etc. Examples of sensor categories include biological, environmental, movement, sound, etc.

For cases in which the SP 130 is receiving sensor data associated with a plurality of persons at different locations, the sensor data received includes a client identifier for identifying the individual being supervised. For cases in which the SP 130 is receiving sensor data from a single sensor for a plurality of individuals at the same location, the system uses recognition techniques to identify the individual being sensed and provides the appropriate client identifier with the sensor data. For example, it is know to automatically recognize an individual by voice recognition and facial features. U.S. Pat. No. 6,421,453, entitled "Apparatus and Method for User Recognition Employing Behavioral Passwords," already incorporated herein, discloses recognizing individuals by recognition of gestures and biometric features. The recognition process for identification of a n individual and provision of the client identifier is done by the sensor, user interface or SP 130 as per design choice.

At step (225) the SP checks the compressed digitized data for recognizing the occurrence of an event. Examples of events are: a) a change in an environmental condition; b) a change in the biological condition of the individual; c) an occurrence in the schedule of the individual; d) an expected occurrence in the schedule of the individual, in which the above causes a possible influence on the hygiene, comfort, safety or well being of the person; e) movement of an object; f) locomotion of the person; and g) movement of the person relative to specific objects. The SP 130 is capable of recognizing specified types of events for each individual mentally ill person being supervised. For example, supervision of an individual with Alzheimer's Disease or mental retardation requires recognition of movement of objects for determining when an object is placed in an inappropriate place. Supervision of a person with depression does not require recognition of movement of an object, unless it is an object that could be used in a dangerous way, such as in a suicide attempt.

System 100 supervises persons having different types and levels of mental illness. The user decides what type of supervision is needed and to what degree. Therefore, in the preferred embodiment, the sensors used, types of events recognized and analyzed and assistance provided will vary with each user. For example, a mentally ill person with medical issues may require use of every feature of the system. A person in the beginning stages of Alzheimer's may require monitoring of safety related events and misplaced objects as well as monitoring of the progression of the disease. Minimal features of the to system 100 can be used by the caretaker of a person such as a diabetic child having a very full daily schedule of medications, feedings and blood tests.

At step 230 the SP 130 receives requests from users and mentally ill persons on a real time basis. The SP analyzes the recognized events and processes the requests. The analyzed events provide information necessary for processing the requests.

At step (235) the SP 130 generates answers and recommendations relative to the recognized events and the requests.

Figure 4:
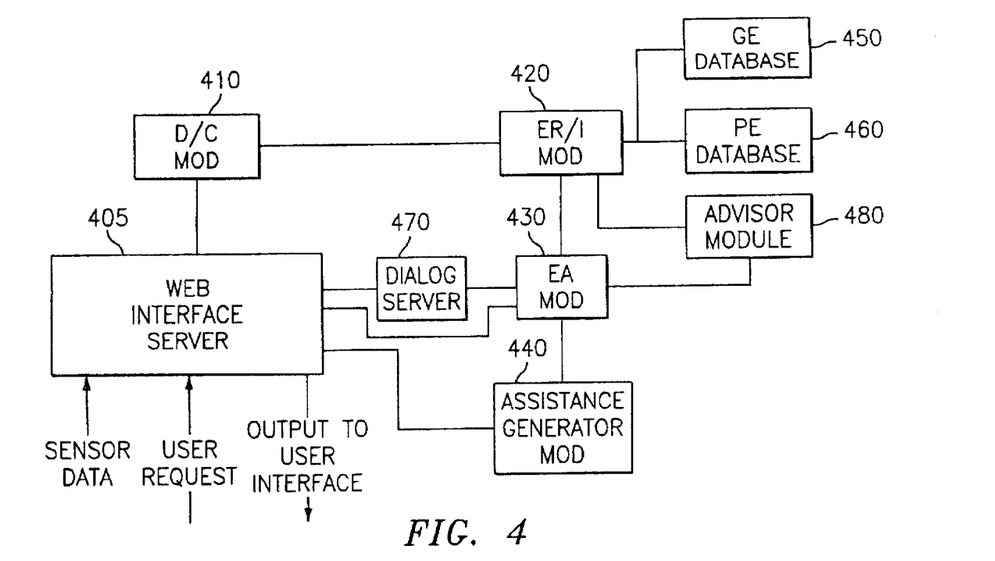
FIG. 4 is a block diagram of the Supervision Provider Server according to the preferred embodiment of the present invention.

Referring to FIG. 4, the basic modules of the SP 130 are shown. The sensor data sent to and information sent from the SP 130 is handled by a server, such as Web Interface Server 405. Preferably, the information sent over the Internet is secured via encryption/decryption techniques such as Secure Sockets Layer (SSL). The sensor data is passed to the digitizer/compressor (D/C) module 410. The D/C module 410 digitizes, compresses and formats the sensor data.

The compressed data is passed to the Event Recognizer/Identifier (ER/I) module 420 that recognizes and identifies the occurrence of events within the compressed data. The ER/I 420 is in communication with a General Events (GE) database 450 and/or a Personal Event (PE) database 460. The recognized events are passed to the Event Analyzer (EA) module 430, which also receives user requests via the Web Interface Server 405. The EA module 430 analyzes the recognized events and processes the requests. The results of the analysis are passed to the Assistance Generator (AG) module 440 generating recommendations and information. The output from the AG module 440 is passed to the Web Interface Server 405 for transmission to the user interface 120.

The GE database 450 is either a database accessible by the SP 130, or is included in the SP 130. The GE database 450 is a collection of event data associated with possible events that might occur, each event being stored in a record. The GE database 450 is divided into sections for storing data relating to objects, human physical conditions, environmental conditions, and human actions. For each event stored a field is provided for storing acceptable values for event data. For example, a blood pressure event record stored in the human physical conditions section includes a field for acceptable blood pressure ranges for people of various sizes and ages, as well as acceptable rates of blood pressure change. An object record stored in the object section includes a field for appropriate locations for the object to be placed, as well as a field for dangerous locations for the object to be placed. In addition, for each event stored a field is provided for storing recommendations for actions to take for cases in which the event data is out of range. For example, a blood pressure event record includes a recommendation field instructing a caretaker to call a doctor when the event data is within a specified range, and to call an ambulance when the event data is within a second specified range. An object record includes a recommendation field instructing the caretaker or individual to place the object in the appropriate location, as well instructing the user interface to activate an alarm when the object is placed in a dangerous location.

The PE database 460 is a collection of Individual Personal Event (IPE) databases, each IPE storing event data associated with a particular individual. Event data is entered into the IPE via the user interface upon registration, upon initiating a supervision session and on an ongoing basis. Each IPE comprises records storing event data associated with different possible events associated with the individual. Each IPE database is divided into sections for storing data relating to objects, the individual's physical condition, the individual's environment's condition, and the individual's actions. The sections of the IPE database correlate to the sections of the GE database. Likewise, event records of the IPE correlate to event records in the GE for corresponding events. The IPE further comprises a section for storing the individual's expected and actual schedule, and a section for storing related data and identities of people with whom the individual interacts. The event data comprises, for each event, acceptable values for event data for the individual. For example, a blood pressure event record stored in the individual's physical conditions database includes a field for acceptable blood pressure ranges for the particular individual, as well as acceptable rates of blood pressure change. An object record stored in the object database includes a field for appropriate and desired locations for the object to be placed, as well as a field for dangerous locations for the object to be placed.

A Dialogue server 470 in communication with the web interface server 405 and the EA 430, is provided. The Dialogue server 470 resolves ambiguities in user requests by determining when a user request is incomplete and when additional information is needed. The Dialogue server 470 requests the additional information via the web interface server 405.

The function of the ER/I 420 will now be discussed in detail. The ER/I 420 reviews the data received from sensors associated with a mentally ill person for detecting the occurrence of an event. The ER/I 420 proceeds according to the category of the sensor data for determining the occurrence of an event. Examples of methods for detection of the occurrence of an event include: object recognition; tracking movement of objects; tracking movement of the person; tracking the time of an occurrence or expected occurrence in the individual's schedule; and tracking changes in the person's condition and the environment's condition.

For sensor data coming from bio-sensors, such as belonging to the category biological data, the ER/I 420 tracks the biological sensor data to check if a significant change has occurred. If so, the ER/I 420 determines that an event has occurred that is related to the condition of the person.

For sensor data coming from environmental sensors such as belonging to the category environmental data, the ER/I 420 tracks the environmental sensor data to check if a significant change has occurred. If so, the ER/I 420 determines that an event related to the environmental condition has occurred.

For sensor data coming from video imaging, such as belonging to the category movement data, the ER/I 420 tracks the objects and mentally ill person to check if a significant change has occurred. A method for identifying and tracking objects is disclosed in U.S. Pat. No. 6,377,296, entitled "A Virtual Map System and Method for Tracking Objects," having the same assignee, which is incorporated herein by reference. It is possible to trace the person's position using the same aforementioned method. If a change of location of an object was detected, the ER/I determines that an object moved event has occurred. If a change of the location of the person was detected, the ER/I 420 determines that an event related to movement of the person has occurred.

For the case in which multiple persons are tracked within the sensor data provided by one source, each person is identified at the start of a session. Identification is performed either by manual entry or automatically, such as by biometric recognition techniques.

The ER/I 420 must identify the object moved and store its new location. The location is stored in terms of coordinates as well as position relative to another object. The ER/I 420 must store the new location of the person, which moved. The location is stored in terms of coordinates as well as position relative to another object.

The ER/I 420 identifies objects by consulting the IPE database for the person being supervised and/or the GE database 450. The IPE database stores data on objects in the environment of the person. By consulting the IPE database and using tracking methods, the ER/I 420 is able to identify relevant objects. Relevant objects are objects which were moved and objects located relative to the moved object or the person which moved.

The ER/I 420 tracks the audio sensor data, other than user requests processed by the user interface 120, to determine if an event has occurred. Audio data may correspond with events relating to the physical condition of the person or the environmental condition.

The ER/I 420 tracks the schedule of the person by checking the schedule of expected schedule events in the person's personal data and recognizing the occurrence of schedule events. Schedule events include, for example, eating, sleeping, waking up, medication schedule, etc. The EI/T 420 recognizes the occurrence of schedule events, for example, by correlating the movement of the individual relative to an object. Examples of correlations include person sitting at table with food to determine an eating event and person laying on bed without significant movement to determine a sleeping event. Other sensors, such as biological sensors, can be used to determine the occurrence of schedule events.

The determination of what constitutes a significant change is provided by default parameters, which are changeable by the user or the system operator.

Upon determination of an occurrence of an event, the most recent sensor data values are stored in order to facilitate tracking and relevant event data, including most recent and previous sensor data values, is forwarded to the EA 430.

Figure 5:
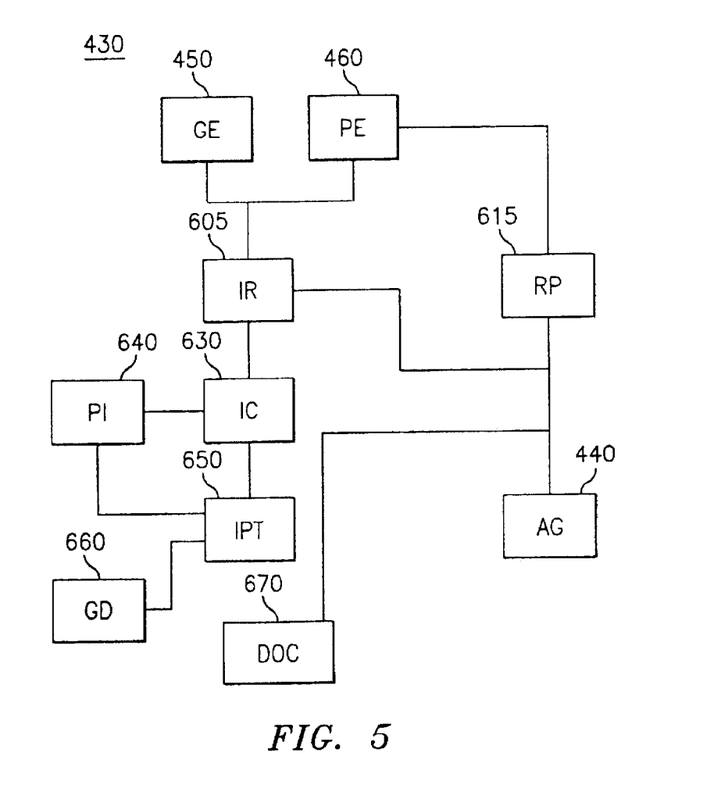
FIG. 5 is a block diagram of the Event Analyzer according to the preferred embodiment of the present invention.

Referring to FIG. 5, the EA 430 and its modules are shown. The EA 430 receives the relevant event data from the ER/I 420 and user requests from the Web Interface Server 405 as real time inputs. The EA 430 processes the inputs as it receives them. Urgent events and requests are given priority for being processed first.

The EA 430 comprises an Incident Recognizer (IR) Module 605 that determines the occurrence of an incident. An incident is an event in which the sensor data values are not equal to expected values stored in the GE 450 or PE 460. The IP 605 compares the relevant event data received to the acceptable values for the event stored in the GE 450 and/or PE 460. If the received data is within range of the acceptable values, an incident has not occurred and the IR 605 continues to process incoming input. When the received data is out of range of the acceptable values, the IR 605 determines that an incident has occurred and retrieves the recommendation associated with the event stored in the GE 450 or PE 460. The recommendations are passed to an Assistance Generator (AG) module 440. The received relevant event data is passed to an Incident Classifying (IC) module 630 for analysis of the event that produced out of range data.

The incident classifying module 630 classifies the recognized incident. The classes are designated to be as broad or narrow as desired. The classes are designated by the system operator and/or user. For example, a class of dangerous incidents is updated and maintained. A Personal Incident (PI) database 640, preferably linked to the IPE database of the mentally ill person, is provided for each mentally ill person for storing data pertaining to each incident that occurred in relation to the person. The IC 630 updates the PI database 640 of the mentally ill person associated with the incident and notifies an Illness Progression Tracking module (IPT) 650. Optionally, the incident can be stored in a general incident database to be used for general analysis.

A General Disease (GD) database 670 is provided for storing data relating to medical histories profiles. The GD database 670 is either included in the SP 130 or is accessible by the SP 130. The IPT module 650 consults the updated PI database 640 and the GD database 670. According to medical criteria, including the information stored in the General Disease database, the IPT module 650 determines the progression of the disease of the mentally ill person and creates a report. Periodically, the IPT module 650 reviews the personal incident database 640 for tracking progression and regression of the disease.

The Request Processor (RP) module 615 determines what has been requested and retrieves the information requested from the section of the GE database 450 or PE database 460 corresponding to the classification of the request.

The following are examples of types of requests and the processing of the requests by the RP 615. For a request to find a misplaced object, the RP 615 looks the object up in the IPE database and retrieves the current location of the object. A recommendation to find the object at the current location is generated. For a request to perform a calculation, the RP 615 develops a formula to perform the calculation. The calculation can be performed by the RP 615 or by the Assistance Generator 440. For a request stating that the person does not feel well, the RP 615 consults the current values stored in the PE 460 individual's condition, the environmental condition, and the individual's actual and expected schedule sections. The IR 605 checks if the values are out of range, and if so, recommendations are retrieved from the event records associated with out of range data which are correlated to the person's ill feelings. If no event values are out of range, an appropriate recommendation is generated such as playing soft, relaxing music or drinking tea. For a request regarding the person's schedule, the actual and expected schedule are consulted and recommendations are generated accordingly.

For a request to identify a person, the person identities section is consulted and biometric recognition methods are used. Upon recognition, a recommendation containing the identity of the person is generated. For a request of an appropriate reply to a current situation, a database of statements and appropriate replies is consulted. A recommendation containing the appropriate reply(s) is generated.

The Assistance Generator (AG) module 440 receives recommendations from the IR 605 and the RP 615 of the EA 430. The Assistance Generator Module 440 retrieves from a library or produces the assistance suggested in the recommendations and passes it to the Web Interface Server 405. For example, the recommendation may be to give the person instructions, to play soothing music to the person, to activate an alarm or to activate a device. The AG 440 retrieves an appropriate text message, music file, activate device message etc. from a library and passes it to the Web Interface Server 405 in the appropriate format.

The EA 430 further comprises a Determination of Compliance (DOC) module 670 to determine whether or not the mentally ill person has complied with the recommendations provided. If not, the EA 430 will need to check the classification of the incident to determine whether or not it is dangerous. If the incident is dangerous, an alert must be generated to the mentally ill person and/or his caretaker. If the incident is not dangerous, reminders are generated for aiding the mentally person to fulfill the recommendations.

The DOC 670 maintains a list of the recommendations, each entry on the list further comprising a set of expected sensor data values for confirming compliance with the recommendation. The DOC periodically compares the expected sensor values to the current sensor values to determine compliance. Entries are removed from the DOC list once they have been complied with.

In the preferred embodiment, the system 100 provides navigational assistance, such as GPS, to mentally ill persons for assisting them with their travels. The navigational assistance is provided by including navigational sensors to accompany the person on his travels. Furthermore, the SP 130 comprises a navigating module for processing the navigational sensor data, consulting a database of geographical information, and providing directions.

In the preferred embodiment, the system provides means for monitoring the medicinal intake of the patient for insuring proper care. Accurate supervision is critical, as a mentally ill person may attempt to trick the system into thinking that a medication was taken, when it was not. U.S. Pat. No. 6,418,423, entitled "Method and Apparatus for Executing Neural Network Applications on a Network of Embedded Devices," of the same assignee, which is incorporated herein by reference, discloses an apparatus which could be employed for medicinal intake supervision. U.S. Pat. No. 6,238,337, entitled "Medical Non-Intrusive Prevention Based on Network of Embedded Systems," of the same assignee, is also incorporated herein by reference.

It is contemplated that the SPS is in communication with an artificial intelligence processor for applying artificial intelligence to the processes performed by the SPS. It is further contemplated that Intelligent Agents are communicating with the SPS at the various stages of processing information.

While the invention has been shown and described with reference to a certain preferred embodiment thereof, it will be understood by those skilled in the art that various changes in form and detail may be made therein without departing from the spirit and scope of the invention as defined by the appended claims.

What is claimed is:

1. A system for supervising persons with a mental illness, the system comprising:
    at least one sensor means for sensing physical properties relating to a person and the person's environment, the sensor means outputting sensor data, the sensor data at least providing an indication of one or more actions of the person;
    a Supervision Provider Server receiving the sensor data; the Supervision Provider Server comprising:
        means for continuously tracking the sensor data and updating a profile associated with the person according to the sensor data; and
        means for recognizing a change in the sensor data indicating the occurrence of an event, the event including one or more actions of the person, wherein if the one or more actions are determined to be unacceptable, notifying the person and providing assisting instructions to the person to correct the unacceptable action.

2. The system according to claim 1, the Supervision Provider Server further comprising:
    an event database storing a collection of event data entries, each entry comprising identification of one of the sensor means, identification of the entity being sensed by the sensor means and predetermined allowable values for the sensor data;
    means for recognizing the occurrence of an incident, upon recognizing the occurrence of the event, by consulting the event database and determining when the received sensor data is outside of a range of the stored allowable sensor data values; and
    means for outputting an indicator of an occurrence of an incident.

3. The system according to claim 2, wherein the Supervision Provider Server receives requests for information related to recognized events, and wherein the Supervision Provider Server further comprises:
    means for processing the requests,
    means for retrieving the information requested from the event database, and
    means for outputting the retrieved information.

4. The system according to claim 3, further comprising a user interface in communication with the Supervision Provider Server for receiving user entries and the sensor data from the sensor means and providing the sensor data to the Supervision Provider Server, for receiving requests from a user and providing the requests to the Supervision Provider Server, and for receiving outputs from the Supervision Provider Server.

5. The system according to claim 4, wherein each sensor data entry in the event database further comprises a recommendation for actions to be taken when the received sensor data is out of range from the allowable sensor data;
    wherein the Supervision Provider Server further comprises means for retrieving a stored recommendation upon recognition of the occurrence of an incident.

6. The system according to claim 4 wherein the user interface is in communication with the Supervision Provider Server via the Internet.

7. The system according to claim 6, wherein the Supervision Provider Server further comprises a Web Interface Server for receiving data from and transmitting data to the user interface.

8. The system according to claim 4, wherein the Supervision Provider Server further comprises a Dialogue Server for resolving ambiguities and needs for additional information in user requests by transmitting dialogue requests to the user interface for additional information.

9. The system according to claim 5, wherein the Supervision Provider Server further comprises:
    means for generating assistance, wherein the means for generating assistance receives a recommendation from the event database; and
    wherein the means for generating assistance provides assistance requested in the recommendation to the user interface by one of creating the assistance and retrieving the assistance from a library.

10. The system according to claim 9, wherein the assistance comprises one of a text message, music, graphics, instructions to a device or instructions to the user.

11. The system according to claim 10, wherein the Supervision Provider Server further comprises a means for determining compliance for determining that instructions provided to the user interface have been complied with;
    wherein the means for determining compliance maintains a list of entries of instructions provided to the user interface; the list comprising a list of expected sensor data values indicating compliance; and
    the means for determining compliance comparing values of current sensor data received to the expected sensor data values for determining compliance, and removes each entry from the list for which compliance has been determined.

12. The system according to claim 2, wherein the event database comprises: a general event database for storing event data entries relating to a general population.

13. The system according to claim 12, wherein the event database further comprises:
- a personal event database for storing event data relating to the person and the person's environment, and wherein each event data entry further comprises the most recent sensor data received from the sensor means; and
- means for updating each event data entry of the personal event database.

14. The system according to claim 13, wherein a subset of the event data entries comprise schedule entries for storing data relating to the schedule of the person, the schedule entries comprising the expected time of occurrence for a scheduled event, the actual time of occurrence of a scheduled event, and an identification of the scheduled event.

15. The system according to claim 2 wherein the Supervision Provider Server further comprises:
- means for assigning a classification to each incident, which occurs;
- a personal incident database for storing incident data for the person, wherein an incident data comprises the incident classification, a count of the number of occurrences of the incident in the classification, and times of occurrences; and
- means for updating the personal incident database upon recognition of the occurrence of an incident.

16. The system according to claim 15, wherein the Supervision Provider Server further comprises:
- a general disease database storing medical history data comprising incident data for stages in progressions of historical occurrences of diseases; and
- means for illness progression tracking, wherein the means for illness progression tracking compares the incident data in the personal incident database to incident data in the general disease database for determining when recognized incidents indicate progression of the person's disease to a different stage.

17. The system according to claim 2, wherein the sensor means is a camera, the sensor data comprises at least one of visual data and audio data, the visual data comprises a coordinate location of an object sensed and a relative location of the objects relative to a different object.

18. The system according to claim 17, wherein the allowable values for the visual data comprise a predetermined allowable coordinate location, and an allowable relative location.

19. The system according to claim 1, wherein the sensor means include navigational sensors; and
- wherein the Supervision Provider Server further comprises a navigating module for processing the navigational sensor data, consulting a database of geographical information and providing navigational directions to a user of the system.

20. The system according to claim 1, wherein the Supervision Provider Server comprises a medicinal intake supervision module for processing sensor data related to medicinal intake.

21. A method for supervising a person with a mental illness, the method comprising the steps of:
(a) acquiring sensor data related to the person and the person's environment, the sensor data at least providing an indication of one or more actions of the person;
(b) continuously tracking the acquired sensor data and updating a profile associated with the person according to the sensor data; and
(c) recognizing changes in the sensor data indicating the occurrence of an event, the event including one or more actions of the person, wherein if the one or more actions are determined to be unacceptable, notifying the person and providing assisting instructions to the person to perform a corrective action.

22. The method according to claim 21, further comprising the steps of:
(d) acquiring access to an event database of stored event data entries, each event data entry comprising identification of the sensor data, identification of the entity being sensed and allowable values for the sensor data;
(e) recognizing the occurrence of an incident in which the received sensor data is outside of the range of the stored allowable sensor data values.

23. The method according to claim 22, further comprising the steps of:
(f) receiving requests for information related to recognized events;
processing the received requests;
(g) retrieving information requested from the event database; and outputting the retrieved information.

24. The method according to claim 23, wherein the acquired sensor data is submitted to a service provider, and wherein the service provider performs steps (b)–(g) for a fee.

25. The method according to claim 22, wherein:
each stored event data entry further comprises a recommendation for assistance providing actions to be taken when the received sensor data is out of range from the allowable sensor data; and
further comprising the step of retrieving a stored recommendation upon recognition of the occurrence of an incident.

26. The method according to claim 25, further comprising the steps of:
acquiring access to a library of assistance files wherein the assistance files store text messages, instructions to devices, music, graphics and instructions to a user;
providing assistance requested in the retrieved recommendation to a user interface by one of creating an assistance file or retrieving an assistance file from the library of assistance files.

27. The method according to claim 26, further comprising the steps of:
determining compliance with instructions to the user and instructions to devices comprising the steps of:
maintaining a list of entries of instructions provided to the user interface;
including with each entry a list of expected sensor data values indicating compliance with the instruction entry;
comparing current sensor data values to expected sensor data values for each instruction entry to determine compliance with the instruction, and
removing the instruction entry from the list upon determination of compliance.

28. The method according to claim 22, further comprising the step of:
assigning a classification to each incident, which occurs;
acquiring access to a personal incident database for storing incident data for the person, wherein the incident data comprises the incident classification and a count of the number of occurrences of an incident in the classification and times of occurrences; and
updating the personal incident database upon recognition of the occurrence of an incident.

29. The method according to claim 28, further comprising the steps of:

acquiring access to a general disease database storing medical history data comprising incident data for stages in progressions of historical occurrences of diseases;

tracking the progression of the person's illness by comparing the incident data in the personal incident database to incident data in the general disease database, and determining when recognized incidents indicate that the person's illness has progressed to a different stage.

30. The method according to claim 22, wherein the event data base further comprises a database of geographical information;

the method further comprising the steps of:

acquiring navigational sensor data from navigational sensors;

processing the navigational sensor data;

consulting the database of geographical information and providing navigational directions to a user interface.

31. An article of manufacture comprising:

a computer usable medium for causing a computer to supervise a mentally ill person, said article having:

computer readable program code means for causing said computer to track sensor data from at least one sensor means, the sensor data relating to a person and the person's environment, the sensor data at least providing an indication of one or more actions of the person; and to recognize changes in the sensor data indicating the occurrence of an event, the event including one or more actions of the person, wherein if the one or more actions are determined to be unacceptable, to notify the person and provide assisting instructions to the person to perform a corrective action, computer readable program code means for causing said computer to acquire access to an event database of stored event data entries, each event data entry comprising identification of one of the sensor means, identification of the entity being sensed by the sensor means, allowable values for the sensor data, and recommendations for assistance providing actions to be taken when the received sensor data is out of range from the allowable sensor data; and recognizing the occurrence of an incident in which the received sensor data is outside of the range of the stored allowable sensor data values;

computer readable program code means for causing said computer to retrieve a stored recommendation upon recognition of the occurrence of an incident;

computer readable program code means for tracking the progression of the person's illness by categorizing the incidents, maintaining a count of the number of occurrences of incidents for each category, and comparing the count to a database of medical histories storing categories of incidents and the counts and rates of increase of numbers of occurrences of the categories of incidents for different stages of progressions of mental illnesses.

32. The computer program product according to claim 31, wherein the computer usable medium further comprises computer readable program code means for:

processing requests from a user interface, wherein the requests are related to recognized events, retrieving the information requested from the event database and outputting the information to the user interface; and providing assistance requested in the retrieved recommendation to a user interface by one of creating an assistance file or retrieving an assistance file from the library of assistance files, wherein an assistance files store text messages, instructions to devices, music, graphics and instructions to a user.

* * * * *